(12) United States Patent
Smith et al.

(10) Patent No.: US 12,257,252 B2
(45) Date of Patent: Mar. 25, 2025

(54) COMPOSITIONS AND METHODS FOR INCREASING TETRAHYDROBIOPTERIN PLASMA EXPOSURE

(71) Applicant: PTC Therapeutics MP, Inc., South Plainfield, NJ (US)

(72) Inventors: Neil Smith, Cary, NC (US); Jonathan Reis, Brookline, MA (US)

(73) Assignee: PTC Therapeutics MP, Inc., Warren, NJ (US)

( * ) Notice: Subject to any disclaimer, the term of this patent is extended or adjusted under 35 U.S.C. 154(b) by 1011 days.

(21) Appl. No.: 17/059,632

(22) PCT Filed: May 30, 2019

(86) PCT No.: PCT/US2019/034515
§ 371 (c)(1),
(2) Date: Nov. 30, 2020

(87) PCT Pub. No.: WO2019/232126
PCT Pub. Date: Dec. 5, 2019

(65) Prior Publication Data
US 2021/0161901 A1    Jun. 3, 2021

Related U.S. Application Data

(60) Provisional application No. 62/822,365, filed on Mar. 22, 2019, provisional application No. 62/771,397, filed on Nov. 26, 2018, provisional application No. 62/677,926, filed on May 30, 2018.

(30) Foreign Application Priority Data

May 28, 2019   (GC) ................................. 2019/37662

(51) Int. Cl.
*A61K 31/519*  (2006.01)
*A61K 9/00*  (2006.01)

(52) U.S. Cl.
CPC .......... *A61K 31/519* (2013.01); *A61K 9/0065* (2013.01)

(58) Field of Classification Search
CPC .............. A61K 31/519; A61K 31/4985; A61K 9/0065; A61P 3/00
See application file for complete search history.

(56) References Cited

U.S. PATENT DOCUMENTS

| | | | |
|---|---|---|---|
| 4,758,571 A | 7/1988 | Curtius et al. | |
| 4,774,244 A | 9/1988 | Curtius et al. | |
| 5,736,343 A | 4/1998 | Landry | |
| 7,566,462 B2 | 7/2009 | Jungles et al. | |
| 7,566,714 B2 | 7/2009 | Oppenheimer et al. | |
| 7,582,799 B2 | 9/2009 | Yoshino et al. | |
| 7,612,073 B2 | 11/2009 | Oppenheimer et al. | |
| 7,727,987 B2 | 6/2010 | Moser et al. | |
| 7,732,599 B2 | 6/2010 | Moser et al. | |
| 7,947,681 B2 | 5/2011 | Oppenheimer et al. | |
| 8,003,126 B2 | 8/2011 | Jungles et al. | |
| 8,067,416 B2 | 11/2011 | Oppenheimer et al. | |
| 8,188,043 B2 | 5/2012 | Cooke et al. | |
| RE43,797 E | 11/2012 | Oppenheimer et al. | |
| 8,318,745 B2 | 11/2012 | Moser et al. | |
| 9,181,254 B2 | 11/2015 | Yoshino et al. | |
| 9,433,624 B2 | 9/2016 | Oppenheimer et al. | |
| 9,492,451 B2 | 11/2016 | Rustomjee et al. | |
| 9,993,481 B2 | 6/2018 | Oppenheimer et al. | |
| 11,072,614 B2* | 7/2021 | Levy .......................... | A61P 3/00 |
| 11,130,760 B2 | 9/2021 | Yoshino et al. | |
| 11,173,158 B2 | 11/2021 | Hasegawa et al. | |
| 11,752,154 B2* | 9/2023 | Levy ...................... | A61K 38/40 |
| | | | 514/249 |
| 11,773,097 B2* | 10/2023 | Levy ...................... | A61P 25/00 |
| | | | 514/249 |
| 2005/0197341 A1 | 9/2005 | Woolf et al. | |
| 2006/0040946 A1 | 2/2006 | Oppenheimer et al. | |
| 2007/0270581 A1 | 11/2007 | Jungles et al. | |
| 2008/0075666 A1 | 3/2008 | Dudley et al. | |
| 2010/0130500 A1 | 5/2010 | Kakkis | |
| 2011/0144117 A1 | 6/2011 | Widmann et al. | |
| 2013/0108694 A1 | 5/2013 | Chou et al. | |
| 2013/0197000 A1 | 8/2013 | Hasegawa et al. | |
| 2013/0237543 A1 | 9/2013 | Oppenheimer et al. | |
| 2013/0336975 A1 | 12/2013 | Dutzar et al. | |
| 2017/0000793 A1 | 1/2017 | Oppenheimer et al. | |
| 2017/0307591 A1 | 10/2017 | Woolf et al. | |
| 2019/0308975 A1 | 10/2019 | Levy | |
| 2020/0009145 A1 | 1/2020 | Hasegawa et al. | |

(Continued)

FOREIGN PATENT DOCUMENTS

| JP | 2010/523708 A | 7/2010 |
|---|---|---|
| WO | WO-2005/028462 A1 | 3/2005 |

(Continued)

OTHER PUBLICATIONS

Phenylketonuria, 2024, https://phenylketonurianews.com/2021/02/18/what-is-bh4-why-is-it-important-phenylketonuria/#:~:text=BH4%20may%20help%20these%20pieces,treat%20some%20people%20with%20PKU.*

(Continued)

*Primary Examiner* — Sun Jae Yoo

(74) *Attorney, Agent, or Firm* — Clark & Elbing LLP

(57) ABSTRACT

The present invention features compositions including sepiapterin, or a pharmaceutically acceptable salt thereof, and methods for the treatment of BH4-related disorders. In some embodiments, these compositions and methods result in an increase in plasma exposure of BH4.

13 Claims, 2 Drawing Sheets

(56) References Cited

U.S. PATENT DOCUMENTS

| | | | |
|---|---|---|---|
| 2020/0010469 A1 | 1/2020 | Yoshino et al. | |
| 2020/0061070 A1 | 2/2020 | Levy | |
| 2021/0269443 A1* | 9/2021 | Levy | C07C 65/05 |
| 2022/0362249 A1* | 11/2022 | Smith | A61P 3/00 |
| 2024/0043426 A1* | 2/2024 | Levy | A61P 43/00 |
| 2024/0100054 A1* | 3/2024 | Levy | A61K 9/14 |

FOREIGN PATENT DOCUMENTS

| | | |
|---|---|---|
| WO | WO-2008/128049 A2 | 10/2008 |
| WO | WO-2011/132435 A1 | 10/2011 |
| WO | WO-2018/102314 A1 | 6/2018 |
| WO | WO-2018/102315 A1 | 6/2018 |
| WO | WO-2019/046849 A1 | 3/2019 |
| WO | WO-2019/232126 A1 | 12/2019 |
| WO | WO-2019/232130 A1 | 12/2019 |
| WO | WO-2021/026247 A1 | 2/2021 |
| WO | WO-2021/062264 A1 | 4/2021 |

OTHER PUBLICATIONS

Fanet et al., 2021, Current Neuropharmacology, 2021, 19, 591-609.*

Smith et al., 2019, Molecular Genetics and Metabolism, 126, 406-412.*

U.S. Appl. No. 17/342,910, PTC Therapeutics MP, Inc.

U.S. Appl. No. 17/486,421, PTC Therapeutics MP, Inc.

European Medicines Agency, "Guideline on conduct of pharmacokinetic studies in target animal species," dated Nov. 9, 2017 (13 pages).

ClinicalTrials.gov Identifier: NCT03519711, "A Study of CNSA-001 in Primary Tetrahydrobiopterin (BH4) Deficient Participants with Hyperphenylalaninemia," <https://clinicaltrials.gov/ct2/show/study/NCT03519711>, last updated Jan. 5, 2021, retrieved on Feb. 11, 2021 (5 pages).

Extended European Search Report for European Patent Application No. 19810058.8, dated Feb. 14, 2022 (10 pages).

Longo, "Disorders of biopterin metabolism," J Inherit Metab Dis. 32(3):333-42 (2009).

U.S. Appl. No. 17/059,719, PTC Therapeutics MP, Inc.

U.S. Appl. No. 17/059,887, PTC Therapeutics MP, Inc.

"Cerebrospinal fluid," <https://en.wikipedia.org/w/index.php?title=Cerebrospinal_fluid&oldid=836321065>, retrieved Aug. 5, 2019 (8 pages).

Bernegger et al., "High frequency of tetrahydrobiopterin-responsiveness among hyperphenylalaninemias: a study of 1,919 patients observed from 1988 to 2002," Mol Genet Metab. 77(4): 304-13 (2002).

Blau et al., "Tetrahydrobiopterin deficiencies without hyperphenylalaninemia: diagnosis and genetics of DOPA-responsive dystonia and sepiapterin reductase deficiency," Mol Genet Metab. 74(1-2): 172-85 (2001).

Brittain et al., "Polymorphism in Pharmaceutical Solids," CRC Press. 192:3-480 (2016).

Bruschi, "Drug Delivery Systems-Mechanisms of floating, *Strategies to Modify the Drug Release from Pharmaceutical Systems*," Woodhead Publishing Medical. 87 (2015).

Caira M.R., "Crystalline polymorphism of organic compounds." Design of Organic Solids. Topics in Current Chemistry. 198 (1998).

Curtius et al., "Atypical phenylketonuria due to tetrahydrobiopterin deficiency. Diagnosis and treatment with tetrahydrobiopterin, dihydrobiopterin and sepiapterin." Clin Chim Acta. 93(2): 251-62 (1979).

Grant et al., "Relationships among rat ultrasonic vocalizations, behavioral measures of striatal dopamine loss, and striatal tyrosine hydroxylase immunoreactivity at acute and chronic time points following unilateral 6-hydroxydopamine-induced dopamine depletion," Behav Brain Res. 291:361-71 (2015) (24 pages).

Hennermann et al., "Partial and total tetrahydrobiopterin-responsiveness in classical and mild phenylketonuria (PKU)," J Inherit Metab Dis. 25(Suppl 1): 21:041-P (2002) (Abstract only).

Ichiyama et al., "Enzymic studies on the biosynthesis of serotonin in mammalian brain," J Biol Chem. 245(7): 1699-709 (1970).

International Search Report and Written Opinion for International Application No. PCT/US2019/034515, dated Aug. 16, 2019 (25 pages).

Kaufman, "Phenylalanine hydroxylation cofactor in phenylketonuria," Science. 128(3337): 1506-8 (1958).

Klaiman et al., "Tetrahydrobiopterin as a treatment for autism spectrum disorders: a double-blind, placebo-controlled trial," J Child Adolesc Psychopharmacol. 23(5): 320-8 (2013) (11 pages).

Kuplennik et al., "Enhanced nanoencapsulation of sepiapterin within PEG-PCL nanoparticles by complexation with triacetyl-beta cyclodextrin," Molecules. 24(15):2715 (2019).

Kure et al., "Tetrahydrobiopterin-responsive phenylalanine hydroxylase deficiency," J Pediatr. 135(3): 375-8 (1999).

Kwon et al., "Reduced biopterin as a cofactor in the generation of nitrogen oxides by murine macrophages," J Biol Chem. 264(34): 20496-501 (1989).

Matalon et al., "Tetrahydrobiopterin ($BH_4$) responsive phenylalanine hydroxylase (PAH) mutations," J Inherit Metab Dis. 25(Suppl 1): 23:045-P (2002) (Abstract only).

Mayer et al., "Brain nitric oxide snythase is a biopterin- and flavin-containing multi-functional oxido-reductase," FEBS Lett. 288(1-2): 187-91 (1991).

Muntau et al., "Tetrahydrobiopterin as an alternative treatment for mild phenylketonuria," N Engl J Med. 347(26): 2122-32 (2002).

Nagatsu et al., "Tyrosine hydroxylase. The initial step in norepinephrine biosynthesis," J Biol Chem. 239(9): 2910-7 (1964).

Niederwieser et al., "Atypical phenylketonuria with defective biopterin metabolism. Monotherapy with tetrahydrobiopterin or sepiapterin, screening and study of biosynthesis in man," Eur J Pediatr. 138(2): 110-2 (1982).

Park et al., "Optimization of expression conditions enhances production of sepiapterin, a precursor for tetrahydrobiopterin biosynthesis, in recombinant *Escherichia coli*," J Microbiol Biotechnol. 25(10): 1709-13 (2015).

Pfleiderer et al., "Pteridine, LXVIII. Überführung von biopterin in sepiapterin und absolute konfiguration des sepiapterins," Chem Ber. 112: 2750-2755 (1979).

Ponzone et al., "Hyperphenylalaninemia and pterin metabolism in serum and erythrocytes," Clin Chim Acta. 216(1-2): 63-71 (1993).

Saeed et al., "Uncertainty of thermal characterization of phase change material by differential scanning calorimetry analysis," Int J Eng Res Technol. 5(1): 405-12 (2016).

Sawabe et al., "Cellular uptake of sepiapterin and push-pull accumulation of tetrahydrobiopterin," Mol Genet Metab. 94(4): 410-6 (2008).

Sawabe et al., Sepiapterin administration raises tissue BH4 levels more efficiently than $BH_4$ supplement in normal mice, *Chemistry and Biology of Pteridines and Folates*. Ed. Milstien et al., pp. 199-204 (2001).

Schircks et al., "Über Pterinchemie. 65 Mitteilung [1]. Herstellung von (6 R,S)-5,6,7,8-Tetrahydro-L-biopterin, 7,8-Dihydro-L-biopterin, L-Sepiapterin, Deoxysepiapterin, (6 R,S)-5,6-Dihydrodeoxysepiapterin and 2'-Deoxybiopterin," Helv Chim Acta. 61(7): 2731-8 (1978).

Shircks Laboratories, "Data Sheet: L-Sepiapterin. Product No. 11.225," published Jan. 26, 2016 (1 page).

Smith et al., "Phase I clinical evaluation of CNSA-001 (sepiapterin), a novel pharmacological treatment for phenylketonuria and tetrahydrobiopterin deficiencies, in healthy volunteers," Mol Genet Metab. 126(4): 406-12 (2019).

Spaapen et al., "Tetrahydrobiopterin-responsive phenylalanine hydroxylase deficiency, state of the art," Mol Genet Metab. 78(2): 93-9 (2003).

Sugiura et al., "The structures of the reoxidation products of 7,8-dihydroneopterin," Bull Chem Soc Jpn. 46(3): 939-42 (1973).

Tietz et al., "A new pteridine-requiring enzyme system for the oxidation of glyceryl ethers," J Biol Chem. 239(12): 4081-90 (1964).

Viscontini et al., "Fluorescent substances from *Drosophilia melanogaster*. XII. The yellow fluorescent pterine: sepiapterin and isosepiapterin," Helvetica Chimica Acta. 42: 836-41 (1959).

(56) References Cited

OTHER PUBLICATIONS

Woo et al., "Production of sepiapterin in *Escherichia coli* by coexpression of cyanobacterial GTP cyclohydrolase I and human 6-pyruvoyltetrahydropterin synthase," Appl Environ Microbiol. 68(6): 3138-3140 (2002).
"Drug pharmacokinetic test of pharmaceutical products, Drug No. 796," A Chief Administrative Agency for Ministry of Health, Labour, and Welfare. 2001(6) (Jan. 2016) (12 pages).

* cited by examiner

COMPOSITIONS AND METHODS FOR INCREASING TETRAHYDROBIOPTERIN PLASMA EXPOSURE

BACKGROUND OF THE INVENTION

Sepiapterin is a naturally occurring precursor of tetrahydrobiopterin (BH4), a naturally occurring essential cofactor of critical intracellular enzymes including but not limited to phenylalanine hydroxylase (PAH) (Kaufman, 1958), tyrosine hydroxylase (TH) (Nagatsu et al, 1964), tryptophan hydroxylase (TPH) (Ichiyama et al, 1970), nitric oxide synthases (NOS) (Kwon et al, 1989), (Mayer et al, 1991) and alkylglycerol monooxygenase (AGMO) (Tietz et al, 1964). Rapid conversion of sepiapterin to BH4 occurs via a two-step reduction in the salvage pathway for BH4 synthesis (Sawabe, 2008). A synthetic form of BH4 (e.g., sapropterin dihydrochloride) is used as a therapy for diseases associated with high plasma phenylalanine, such as phenylketonuria (PKU). PKU is an inborn error of metabolism caused predominantly by mutations in the PAH gene. BH4 was also tested as a therapy for various central nervous symptoms associated with PKU and other diseases, but demonstrated limited effect, presumably due to the inability of BH4 to cross the blood brain barrier effectively (Klaiman et al, 2013; Grant et al, 2015).

Recent work has suggested that, compared with BH4, peripherally administered sepiapterin possesses greater permeability through membranes and as a result, can more readily access liver, kidney, and brain cells. It is reported that sepiapterin is rapidly converted into BH4 intracellularly, thereby elevating liver, kidney, and brain BH4 levels (Sawabe, 2008). As a result, sepiapterin may serve as a useful therapeutic for diseases associated with low intracellular BH4 levels or with dysfunction of various BH4 dependent metabolic pathways.

SUMMARY OF THE INVENTION

The present invention is directed to the discovery that administration of sepiapterin with food to a subject unexpectedly results in an increase of production of BH4 and resulting BH4 plasma exposure, CSF exposure, and/or brain exposure of the subject. Without being bound by theory, the increase in BH4 plasma exposure may result from a delay in absorption of sepiapterin due to increased gastric residence time or a prolonged rate of absorption of sepiapterin due to increased anterior intestine residence time, or from prolonged intracellular concentrations of sepiapterin below, at, or slightly above the maximum velocity of enzymatic activity ($V_{max}$) for sepiapterin reductase or dihydrofolate reductase, or a combination of the above, resulting in a greater percentage of the administered sepiapterin being converted to BH4 prior to passive or active transport into circulation for excretion and/or elimination. The present invention features compositions including sepiapterin, or a salt thereof, and methods for the treatment of BH4-related disorders. In some embodiments, these compositions and methods result in an increase in plasma exposure of BH4.

As is known in the art, food can influence the absorption of compounds. Absorption may be delayed, but not reduced, or the total amount of the drug absorbed may be reduced. The food effect may be due to slowing gastric residence time, slowing anterior intestine residence time, decreasing access of the compound to absorption sites, altering the dissolution rate of the compound, or altering the pH of the stomach. Because of these effects, it is important that a specific dosage schedule be established for drugs that should be administered apart from meals or with food.

In one aspect, the invention features a method of treating a BH4-related disorder in a subject in need thereof, by administering an effective amount of sepiapterin, or a pharmaceutically acceptable salt thereof, with food.

In another aspect, the invention features a method of increasing the BH4 plasma exposure in a subject receiving sepiapterin therapy by administering to the subject an effective amount of sepiapterin, or a pharmaceutically acceptable salt thereof, with food.

In a further aspect, the invention features a method of reducing the rate of absorption of an oral dosage form of sepiapterin as measured by the concentration of BH4 attained in the plasma over time in a subject in need of a therapeutic effect thereof. The method includes administering to the subject an effective amount of sepiapterin, or a pharmaceutically acceptable salt thereof, with food.

In some embodiments of any of the foregoing methods, the effective amount is an amount (e.g., 2.5 mg/kg to 100 mg/kg per dose) sufficient to produce a BH4 concentration of at least 50 ng/mL (e.g., at least 60 ng/mL, at least 100 ng/mL, at least 200 ng/mL, at least 400 ng/mL, at least 600 ng/mL, at least 1000 ng/mL, or at least 2000 ng/mL) in the plasma of the subject within 10 hours of administration with food. The effective amount may include a dose that is at least 5% (at least 10%, at least 20%, at least 50%, at least 70%, at least 90%, at least 100%, at least 110%, at least 120%, at least 130%, at least 140%, or at least 150%) lower than the dose sufficient to produce a maximum BH4 plasma concentration (Cmax) of at least 50 ng/mL (e.g., at least 60 ng/mL, at least 100 ng/mL, at least 200 ng/mL, at least 400 ng/mL, at least 600 ng/mL, at least 1000 ng/mL, or at least 2000 ng/mL) in the plasma of the subject within 10 hours of administration of sepiapterin without food.

In some embodiments of any of the foregoing methods, administration to the subject occurs less than 30 minutes prior to consuming food or after consuming food, e.g., immediately prior to the consumption of food up to 1 hour after consumption. In some embodiments, the administration to the subject is substantially at the same time as food. In some embodiments of any of the foregoing methods, the food is a high protein food. In some embodiments of any of the foregoing methods, the food is a high fat food (e.g., at least 25, 30, 40, or 50% of the calories are from fat). In some embodiments of any of the foregoing methods, the food is a high protein and high fat food. In some embodiments, the food is high calorie food (e.g., the food includes at least 100 calories, e.g., at least 200 calories, at least 300 calories, at least 400 calories, at least 500 calories, e.g., 500-1500 or 800-1000 calories). In some embodiments of any of the foregoing methods, the food is a meal, e.g., breakfast, lunch, or dinner.

In some embodiments, the administration with food (e.g., occurring less than 30 minutes prior to consuming food or after consuming food, e.g., immediately prior to the consumption of food up to 1 hour after consumption) results in an increase (e.g., at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, or at least 150%) in the Cmax of BH4 compared to administration without food (e.g., occurring more than 2 hours after consuming food until 30 minutes prior to consuming further food).

In some embodiments, the administration with food (e.g., occurring less than 30 minutes prior to consuming food or after consuming food, e.g., immediately prior to the consumption of food up to 1 hour after consumption) results in an increase (e.g., at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, or at least 150%) in the extent of production and resulting plasma exposure ($AUC_{0-last}$) of BH4 compared to administration without food (e.g., occurring less than 30 minutes prior to consuming food or after consuming food, e.g., immediately prior to the consumption of food up to 1 hour after consumption).

In some embodiments of any of the foregoing aspects, the sepiapterin is provided in a separate composition from the consumed food (e.g., the sepiapterin is not incorporated into a food product). In some embodiments of any of the foregoing aspects, the consumption of food occurs prior to the administration of sepiapterin (e.g., the consumption of food occurs between 1 hour up to immediately prior to the administration of sepiapterin). In some embodiments, the consumption of food occurs after the administration of sepiapterin (e.g., the consumption of food occurs between immediately after administration up to 30 minutes after administration).

In a further aspect, the invention features pharmaceutical compositions of sepiapterin, or a pharmaceutically acceptable salt thereof, which mimic the effect of administration with food, e.g., compositions formulated to increase gastric residence time (e.g., formulations described in Radhakrishnan et al. Drug Delivery Letters, 2017, 7, 190-200, the formulations of which are incorporated by reference).

In some embodiments, the composition is formulated as a bio-adhesive dosage form, a high-density dosage form, an expandable dosage form, a super-porous hydrogel dosage form, or a floating dosage form (e.g., a composition including ion exchange resin, a raft system, an inflatable chamber, an effervescent mixture, a swellable hydrocolloid, or a multi-particulate system).

In another aspect, the invention features a method of treating a BH4-related disorder in a subject in need thereof, the method by administering an effective amount of any of the foregoing pharmaceutical compositions.

In yet another aspect, the invention features a method of increasing the BH4 plasma exposure in a subject receiving sepiapterin therapy by administering to the subject an effective amount of any of the foregoing pharmaceutical compositions.

In a further aspect, the invention features a method of delaying or reducing (e.g., reducing by at least 5%, at least 10%, at least 20%, at least 30%, at least 40%, or at least 50%) the rate of absorption of an oral dosage form of sepiapterin as measured by the concentration of BH4 attained in plasma over time in a subject in need of a therapeutic effect thereof, by administering to the subject an effective amount of any of the foregoing pharmaceutical compositions.

In one aspect, the invention features a method of increasing the level of homovanillic acid and/or 5-hydroxyindoleacetic acid in a subject, the method comprising administering an effective amount of sepiapterin, or a pharmaceutically acceptable salt thereof, with food. In some embodiments, the level of homovanillic acid and/or 5-hydroxyindoleacetic acid in the cerebrospinal fluid (CSF) of the subject is increased. In some embodiments, the level of homovanillic acid and/or 5-hydroxyindoleacetic acid in the subject (e.g., in the CSF of the subject) is increased at least 5% compared to the level prior to administration (e.g., the level is increased at least 10%, at least 20%, at least 30%, at least 40%, at least 50%, at least 60%, at least 70%, at least 80%, at least 90%, at least 100%, at least 150%, at least 200%, at least 250%, at least 300% compared to the level prior to administration).

In some embodiments, prior to administration of sepiapterin, or a pharmaceutically acceptable salt thereof, the subject has levels of homovanillic acid and/or 5-hydroxyindoleacetic acid that are less than 50% (e.g., less than 40%, less than 30%) of the levels an average subject, (e.g., the subject has CSF levels of homovanillic acid of less than 15 ng/mL and/or has CSF levels of 5-hydroxyindoleacetic acid of less than 5 ng/mL). In some embodiments, the subject has not been diagnosed with a BH4-related disorder. In some embodiments, the subject does not have symptoms of a BH4-related disorder. In some embodiments, after administration of sepiapterin, or a pharmaceutically acceptable salt thereof, the levels of homovanillic acid and/or 5-hydroxyindoleacetic in the subject are greater than 50% of the levels of an average subject, (e.g., the subject has CSF levels of homovanillic acid of greater than 15 ng/mL and/or has CSF levels of 5-hydroxyindoleacetic acid of greater than 5 ng/mL).

In some embodiments of any of the foregoing aspects, the subject is suffering from and/or been diagnosed with a BH4-related disorder.

In some embodiments of any of the foregoing aspects, the BH4-related disorder is primary BH4 deficiency, GTPCH deficiency, 6-pyruvoyl-tetrahydropterin synthase (PTPS) deficiency, DHPR deficiency, sepiapterin reductase deficiency, dopamine responsive dystonia, Segawa Syndrome, tyrosine hydroxylase deficiency, phenylketonuria, DNAJC12 deficiency, Parkinson's Disease, depression due to Parkinson's Disease, impulsivity in Parkinson's patients, major depression, Autism spectrum, ADHD, schizophrenia, Bipolar disorder, cerebral ischemia, restless leg syndrome, Obsessive Compulsive Disorder, anxiety, aggression in Alzheimer's disease, cerebrovascular disorders, spasm after subarachnoidal hemorrhage, myocarditis, coronary vasospasm, cardiac hypertrophy, arteriosclerosis, hypertension, thrombosis, infections, endotoxin shock, hepatic cirrhosis, hypertrophic pyloric stenosis, gastric mucosal injury, pulmonary hypertension, renal dysfunction, impotence, or hypoglycemia. In some embodiments of any of the foregoing aspects, the BH4-related disorder is phenylketonuria, a BH4 deficiency (e.g., primary BH4 deficiency), a CNS disorder (such as Segawa syndrome, depression, schizophrenia, autism, or Parkinson's disease), or a gastrointestinal motility disorders (such as gastroparesis and primary and secondary esophageal motility disorder). In some embodiments, the BH4-related disorder is a BH4 deficiency or phenylketonuria.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the term "administration" refers to the administration of a composition to a subject. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, or vitreal.

An "effective amount" of a compound may vary according to factors such as the disease state, age, sex, and weight of the individual, and the ability of the compound to elicit the desired response. A therapeutically effective amount encompasses an amount in which any toxic or detrimental effects of the compound are outweighed by the therapeutically beneficial effects. An effective amount also encompasses an amount sufficient to confer benefit, e.g., clinical benefit.

The term "food," as used herein, refers to solid food with sufficient bulk and fat content that it is not rapidly dissolved and absorbed in the stomach. For example, a meal, such as breakfast, lunch, or dinner. The term "with food," as used herein refers to administration of a composition between about 30 minutes prior to about two hours after eating, e.g., eating a meal. The terms "without food," "fasted," or "an empty stomach" refer to the condition of not having consumed solid food for at least about 2 hours until about 30 minutes prior to consuming further solid food.

The term "pharmaceutical composition," as used herein, represents a composition containing a compound described herein formulated with a pharmaceutically acceptable excipient. Pharmaceutical compositions can be formulated, for example, for oral administration in unit dosage form (e.g., a tablet, capsule, caplet, gel cap, suspension, solution, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation. As used herein, the term "pharmaceutically acceptable salt" means any pharmaceutically acceptable salt of sepiapterin. For example, pharmaceutically acceptable salts of sepiapterin include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH 2008. The salts can be prepared in situ during the final isolation and purification of the compounds described herein or separately by reacting a free base group with a suitable organic acid.

Frequently, the compounds are prepared or used as pharmaceutically acceptable salts prepared as addition products of pharmaceutically acceptable acids. Suitable pharmaceutically acceptable acids and methods for preparation of the appropriate salts are well-known in the art. Salts may be prepared from pharmaceutically acceptable non-toxic acids including inorganic and organic acids.

Representative acid addition salts include acetate, adipate, alginate, ascorbate, aspartate, benzenesulfonate, benzoate, besylate, bisulfate, borate, butyrate, camphorate, camphorsulfonate, citrate, cyclopentanepropionate, digluconate, dodecylsulfate, ethanesulfonate, fumarate, gentisate, glucoheptonate, glycerophosphate, glycolate, hemisulfate, heptanate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts.

As used herein, the term "subject" or "patient" refers to any organism to which a compound or composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

The term "BH4-related disorder," as used herein, refers to any disease or disorder that may derive a therapeutic benefit from modulation of the level or activity of BH4. BH4-related disorders to include but not limited to primary BH4 deficiency, GTPCH deficiency, 6-pyruvoyl-tetrahydropterin synthase (PTPS) deficiency, DHPR deficiency, sepiapterin reductase deficiency, dopamine responsive dystonia, Segawa Syndrome, tyrosine hydroxylase deficiency, phenylketonuria, DNAJC12 deficiency, Parkinson's Disease, depression due to Parkinson's Disease, impulsivity in Parkinson's patients, major depression, Autism spectrum, ADHD, schizophrenia, Bipolar disorder, cerebral ischemia, restless leg syndrome, Obsessive Compulsive Disorder, anxiety, aggression in Alzheimer's disease, cerebrovascular disorders, spasm after subarachnoidal hemorrhage, myocarditis, coronary vasospasm, cardiac hypertrophy, arteriosclerosis, hypertension, thrombosis, infections, endotoxin shock, hepatic cirrhosis, hypertrophic pyloric stenosis, gastric mucosal injury, pulmonary hypertension, renal dysfunction, impotence, or hypoglycemia. In some embodiments of any of the foregoing aspects, the BH4-related disorder is phenylketonuria, a BH4 deficiency (e.g., primary BH4 deficiency), a CNS disorder (such as Segawa syndrome, depression, schizophrenia, autism, or Parkinson's disease), or a gastrointestinal motility disorders (such as gastroparesis and primary and secondary esophageal motility disorder). In some embodiments, the BH4-related disorder is a BH4 deficiency or phenylketonuria.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects.

Treatment also includes prolonging survival as compared to expected survival if not receiving treatment.

DETAILED DESCRIPTION

Figure 1:
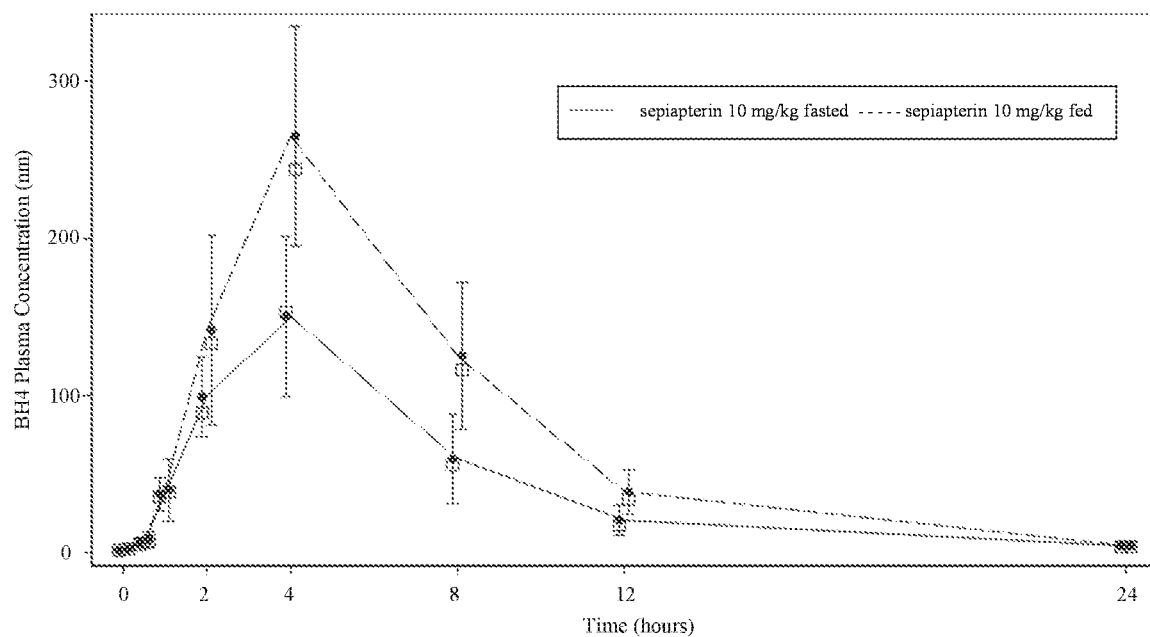
FIG. 1 is a graph illustrating the mean plasma concentration of BH4 over time in fed and fasted subjects.

The present inventors have discovered that administration of sepiapterin, or pharmaceutically acceptable salt thereof, with food unexpectedly results in an increase in the BH4 plasma exposure of a subject. Accordingly, the present invention features compositions including sepiapterin, or a pharmaceutically acceptable salt thereof, and methods for the treatment of BH4-related disorders. These compositions and methods may result in an increase in plasma exposure of BH4.

Sepiapterin

Sepiapterin passes into the cell and is converted to 7,8-dihydrobiopterin by sepiapterin reductase. 7,8-dihydrobiopterin is then converted to BH4 via reduction by dihydrofolate reductase.

Without being bound by theory, administration of sepiapterin with food results in an increase in plasma exposure of BH4, e.g., by reducing the rate of absorption of sepiapterin. If the administered sepiapterin is absorbed quickly, e.g., by being administered on an empty stomach, sepiapterin reductase and/or dihydrofolate reductase in the cells may become saturated above $V_{max}$ resulting in at least a portion of the administered sepiapterin leaving the cell without being reduced to 7,8-dihydrobiopterin and subsequently to BH4. This excess sepiapterin may then be excreted without ever being converted to BH4, resulting in lower levels of BH4 in the plasma compared to administration of sepiapterin with food which reduces the rate of or prolongs the absorption of sepiapterin and results in reaction rates below, at or slightly above the $V_{max}$ for substrate saturation of sepiapterin reductase enzyme and/or dihydrofolate reductase. Administration of sepiapterin with food unexpectedly results in an increase in the maximum BH4 plasma concentration (Cmax) and the extent of exposure as measured by the area under the concentration time curve of time zero to last concentration ($AUC_{0-last}$) of BH4 compared to administration without food.

Sepiapterin has the structure:

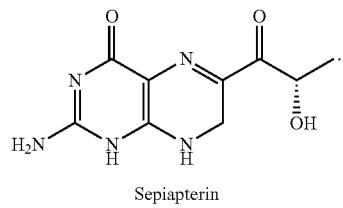

Sepiapterin

Sepiapterin, or a pharmaceutically acceptable salt thereof, can be formulated in a pharmaceutical composition. In some embodiments, a pharmaceutical composition of the invention includes 20-30% sepiapterin, or a salt thereof, by total weight, e.g., 20%, 22%, 25%, 27%, or 30%. In some embodiments, the pharmaceutical compositions include greater than 20% sepiapterin by total weight, e.g., greater than 25%, greater than 30%, greater than 40%, greater than 50%, greater than 60%, greater than 70%, greater than 80%, or greater than 90%. In some embodiments, the pharmaceutical composition includes less than 20% sepiapterin by total weight, e.g., less than 20%, less than 15%, less than 10%, or less than 5%.

In some embodiments, the invention features a pharmaceutical composition including sepiapterin, or a salt thereof, and less than 10% by total body weight of an antioxidant, e.g., 9%, 7%, 5%, 3%, 1%, 0.5%, 0.25%, or 0.1%. The antioxidant may be ascorbic acid. In some embodiments, the ratio of sepiapterin, or a pharmaceutically acceptable salt thereof, to the antioxidant is 1:1, e.g., 2:1, 5:1, 7:1, or 10:1. The pharmaceutical composition may include 20-30% sepiapterin, or a pharmaceutically acceptable salt thereof, by total weight, e.g., 20%, 22%, 25%, 27%, or 30%. The pharmaceutical composition can further include a dispersant, e.g., croscarmellose sodium. The pharmaceutical composition may include 0.1-1.5% dispersant by total weight, e.g., 0.1%, 0.5%, 1%, or 1.5%. In some embodiments, the pharmaceutical composition includes at least one anti-caking agent, e.g., colloidal silicon dioxide or microcrystalline cellulose. The pharmaceutical composition may include 65-75% anti-caking agent by total weight, e.g., 65%, 67%, 70%, 73%, or 75%. In some embodiments, the pharmaceutical composition includes both colloidal silicon dioxide and microcrystalline cellulose. In some embodiments, the pharmaceutical composition includes 60-65% microcrystalline cellulose by total weight and 5-7% colloidal silicon dioxide by total weight. In some embodiments, the crystalline form of sepiapterin is formulated as particles less than 140 μm in size, e.g., 120 μm, 110 μm, 100 μm, 90 μm, 80 μm, 70 μm, 60 μm, 50 μm, 40 μm, 30 μm, 20 μm, 10 μm, or 5 μm. In some embodiments, the pharmaceutical composition includes less than 1% of an impurity such as lactoylpterin, e.g., the composition includes less than 0.9%, less than 0.8%, less than 0.7%, less than 0.6%, less than 0.5%, less than 0.4%, less than 0.3%, or less than 0.2%.

In some embodiments, the sepiapterin is a salt of sepiapterin, e.g., with sulfuric acid, p-toluene sulfonic acid, methane sulfonic acid, benzene sulfonic acid, malonic acid, tartaric acid (e.g., L-tartaric acid), phosphoric acid, gentisic acid, fumaric acid, glycolic acid, acetic acid, or nicotinic acid.

In some embodiments, the sepiapterin, or pharmaceutically acceptable salt thereof, is in crystalline form. The crystalline sepiapterin free base or a crystalline form of a salt of sepiapterin can occur as an anhydrate (e.g., without having any bound water or solvent or hydration or solvation) or as a hydrate, a partial hydrate (e.g., hemihydrate, sesquihydrate, and the like), as a dihydrate, a trihydrate, or the like, wherein the crystalline form binds a water of hydration or a solvent molecule associated with the crystalline form of sepiapterin or salt thereof. In an embodiment, crystalline sepiapterin occurs as a monohydrate or as a hemihydrate.

In some embodiments, sepiapterin is present in a crystalline form. In some embodiments, the crystalline form of sepiapterin is characterized by an X-ray powder diffraction pattern obtained by irradiation with Cu Kα X-rays having peaks expressed as 2θ at least at about 9.7, about 10.2, and about 11.3°. In other embodiments, the crystalline form of sepiapterin is characterized by an X-ray powder diffraction pattern obtained by irradiation with Cu Kα X-rays having peaks expressed as 2θ at least at about 9.7, about 10.2, about 11.3, about 14.0, about 14.6, about 19.9, about 22.2, about 25.3, and about 32.4°.

The present invention provides a pharmaceutical composition including a pharmaceutically acceptable excipient and an effective amount of sepiapterin, or a pharmaceutically acceptable salt thereof.

The pharmaceutically acceptable excipient can be any of those conventionally used and is limited only by chemico-physical considerations, such as solubility and by the route of administration. It will be appreciated by one of skill in the art that, in addition to the following described pharmaceutical compositions, sepiapterin can be formulated as inclusion complexes, such as cyclodextrin inclusion complexes, or liposomes.

The pharmaceutically acceptable excipients described herein, for example, vehicles, adjuvants, excipients, or diluents, are well known to those who are skilled in the art and are readily available to the public. It is preferred that the pharmaceutically acceptable excipient be one which is chemically inert to the sepiapterin and one which has no detrimental side effects or toxicity under the conditions of use.

Formulations which Increase Gastric and/or Anterior Intestine Residence Time

Gastro-retentive drug delivery is an approach with the drug formulation is designed to remain in the stomach longer, e.g., until drug release is complete.

Bioadhesive dosage forms utilize polymers that are capable of adhering to surfaces and result in a controlled release of the drug. The bioadhesive polymers may be anionic (e.g., carboxymethylcellulose, alginic acid, polyacrylic acid, pectin, carrageenan, polycarbophil, or carbomer); cationic (e.g., chitosan, polylysine, or polybrene); or non-ionic (e.g., polyethylene glycol, polyvinylpyrrolidone, dextran, orhydroxypropylmethylcellulose).

High-density dosage forms are designed to sit in the stomach at a lower level than the pyloric sphincter, and thus avoid emptying. Excipients suitable for high-density dosage forms include iron powder, barium sulphate, zinc oxide, and titanium oxide.

Expandable dosage forms are designed to expand in the stomach to be larger than the pyloric sphincter, and thus avoid emptying. For example, dosage forms including a drug core, a swellable hydrocolloid, and an outer semipermeable polymer are suitable for expandable dosage forms.

Super-porous hydrogel dosage forms are designed, similarly to expandable dosage forms, to expand in the stomach to be larger than the pyloric sphincter. Super-porous hydrogel dosage forms may include polymers such as crosscarmellose sodium.

Floating dosage forms are designed to have a lower density than gastric fluid. Floating dosage forms may include compositions including ion exchange resin, a raft system, an inflatable chamber, an effervescent mixture, a swellable hydrocolloid, or a multi-particulate system.

Antioxidants

Sepiapterin is prone to rapid oxidation when exposed to air. Accordingly, pharmaceutical compositions of the invention may include antioxidants. The antioxidant may minimize the oxidative degradation of sepiapterin. Examples of antioxidants include, but are not limited to, ascorbic acid, tocopherol, retinol, ascorbyl palmitate, N-acetyl cysteine, glutathione, ethylenediaminetetraacetic acid, sodium bisulfite, sodium metabisulfite, thiourea, butylatedhydroxytoluene, butylatedhydroxyanisole, and vitamin E. In some embodiments, the pharmaceutical compositions of the invention include ascorbic acid, tocopherol, retinol, ascorbyl palmitate, N-acetyl cysteine, glutathione, butylatedhydroxytoluene, and/or butylatedhydroxyanisole as antioxidant.

In some embodiments, the pharmaceutical composition includes less than 10% antioxidant by weight, e.g., less than 9%, less than 8%, less than 7%, less than 6%, less than 5%, less than 4%, less than 3%, less than 2%, less than 1%, or substantially free of antioxidant. In some embodiments, the pharmaceutical composition includes 2-9% antioxidant by total weight, e.g., 2-4%, 3-5%, 4-6%, 5-7%, 6-8%, or 7-9%. In some embodiments, the pharmaceutical composition comprises 5-100% of the USP maximum daily dose of the antioxidant, e.g., in some embodiments, the pharmaceutical composition comprises 5%, 10%, 15%, 20%, 30%, 40%, 50%, 60%, 70%, 80%, 90%, or 100% of the USP maximum daily dose of the antioxidant. In some embodiments, the ratio of sepiapterin to antioxidant is at least 1:1, e.g., 2:1, 3:1, 4:1, 5:1, 6:1, 7:1, 8:1, 9:1, or 10:1.

Dispersants

In some embodiments, the pharmaceutical compositions of the invention include at least one dispersant. The dispersant may cause particles in the formulation to separate, e.g., release their medicinal substances on contact with moisture. Examples of dispersants include, but are not limited to, crosslinked polyvinylpyrrolidone, carboxymethylcellulose (e.g., croscarmellose salt, e.g., croscarmellose sodium), starch (e.g., sodium starch glycolate), or alginic acid. In some embodiments, the dispersant in the pharmaceutical composition is a carboxymethylcellulose such as a pharmaceutically acceptable salt of croscarmellose. In some embodiments, the pharmaceutical composition may include 0.1-1.5% dispersant by total weight, e.g., 0.1%, 0.5%, 1%, or 1.5%. In some embodiments, the pharmaceutical composition includes less than 1.5% dispersant, e.g., less than 1%, less than 0.5%, or less than 0.1%.

Anti-Caking Agents

In some embodiments, the pharmaceutical compositions of the invention include at least one anti-caking agent. In some embodiments, the pharmaceutical compositions include at least two anti-caking agents. Exemplary anti-caking agents include colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, and polydimethylsiloxane. In some embodiments, the at least one anti-caking agent is colloidal silicon dioxide or microcrystalline cellulose. In some embodiments, the pharmaceutical composition may include 65-75% anti-caking agent by total weight, e.g., 65%, 67%, 70%, 73%, or 75%. In some embodiments, the pharmaceutical composition includes both colloidal silicon dioxide and microcrystalline cellulose. In some embodiments, the pharmaceutical composition includes 60-65% microcrystalline cellulose by total weight and 5-7% colloidal silicon dioxide by total weight.

Dosing Vehicle

In some embodiments, the pharmaceutical compositions of the invention are combined with a dosing vehicle prior to administration, e.g., a dosing vehicle with a viscosity of approximately 50-1750 centipoise (cP). One type of suspending agent that can be used is a combination of glycerin and sucrose in water (e.g., MEDISCA® oral mix with 2.5% glycerin and 27% sucrose in water). An appropriate quantity of composition can be added to the dosing vehicle mixture and agitated to suspend the composition just prior to administration.

Other suspending agents may also be used as a dosing vehicle. Exemplary suspending agents include agar, alginic acid, sodium carboxymethyl cellulose, carrageenan, dextrin, gelatin, guar gum, hydroxyethyl cellulose, hydroxypropyl cellulose, hypromellose, methyl cellulose, polyethylene glycol, povidone, tragacanth, xanthan gum, or other suspending agents known in the art.

Dosage

Sepiapterin, or pharmaceutically acceptable salt thereof, can be used in any suitable dose. Suitable doses and dosage regimens can be determined by conventional range finding techniques. Generally treatment is initiated with smaller dosages, which are less than the optimum dose. Thereafter, the dosage is increased by small increments until optimum effect under the circumstances is reached. For convenience, the total daily dosage may be divided and administered in portions during the day if desired. In proper doses and with suitable administration of certain compounds, the present invention provides for a wide range of responses. Typically, the dosages range from about 2.5 to about 150 mg/kg body weight of the patient being treated/day. For example, in embodiments, sepiapterin, or pharmaceutically acceptable salt thereof, may be administered from about 20 mg/kg to about 150 mg/kg, from about 40 mg/kg to about 100 mg/kg, from about 100 mg/kg to about 150 mg/kg, from about 60 mg/kg to about 120 mg/kg, from about 80 mg/kg to about 100 mg/kg, from about 40 mg/kg to about 60 mg/kg, from about 2.5 mg/kg to about 20 mg/kg, from about 2.5 mg/kg to about 10 mg/kg, or from about 2.5 mg/kg to about 5 mg/kg, of subject body weight per day, one or more times a day, to obtain the desired therapeutic effect.

In some embodiments, the dose is an amount sufficient to produce levels of BH4 in the CNS (e.g., brain), e.g., as measured in the CSF and/or sufficient to produce a therapeutic result and/or response, e.g., increased levels of serotonin or dopamine in the CNS. In some embodiments, an increase in BH4 in the CNS is measured by determining the level of metabolites of a monoamine, e.g., serotonin and/or dopamine (e.g., homovanillic acid or 5-hydroxyindoleacetic acid (5-HIAA)) in the CSF, wherein an increase of metabolites in the CSF indicates an increase in BH4 levels in the CNS (e.g., brain). In some embodiments, the dose is an amount sufficient to increase levels of BH4 at least two times greater (e.g., at least 10 times greater, at least 20 times greater, at least 50 times greater, at least 100 times greater, or at least 150 times greater) than the levels of BH4 prior to administration as measured in the plasma or an organ of the subject, e.g., the liver of the subject.

In some embodiments, the sepiapterin, or pharmaceutically acceptable salt thereof, can be formulated into unit solid oral dosage forms such as particles. In these embodiments, each unit solid oral dosage form can comprise any suitable amount of the sepiapterin, or pharmaceutically acceptable salt thereof. For example, each solid oral dosage form can comprise about 2.5 mg, about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg.

Sepiapterin, or a pharmaceutically acceptable salt thereof, can be used in the preparation of liquid formulations, such as in the form of a solution, suspension, or emulsion. Formulations suitable for oral administration can consist of (a) capsules, sachets, tablets, lozenges, and troches, each containing a predetermined amount of the active ingredient, as solids or granules; (b) powders; (c) liquid solutions, such as an effective amount of the compound dissolved in diluents, such as water, saline, or orange juice; (d) suspensions in an appropriate liquid; and (e) suitable emulsions. Preferred are solid oral dosage forms such as capsule forms, tablet forms, and powder forms. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for oral and/or parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical excipient, such as a sterile liquid or mixture of liquids, including water, saline, aqueous dextrose and related sugar solutions, an alcohol, such as ethanol, benzyl alcohol, or hexadecyl alcohol, glycols, such as propylene glycol or polyethylene glycol and other polyethylene alcohols, glycerol ketals, such as 2,2-dimethyl-1,3-dioxolane-4-methanol, ethers, such as polyethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

The present invention features pharmaceutical compositions in an orally tolerable formula that contains a therapeutically effective amount of sepiapterin and less than 10% antioxidant. In some embodiments, the pharmaceutical composition is a granular formulation that is dispersed in a pharmaceutically acceptable excipient, for example the composition can be mixed into water and ingested by a patient (e.g., over the course of 5 to 10 minutes). Suitable formulations for use in the present invention are found in Remington's Pharmaceutical Sciences, Mack Publishing Company, Philadelphia, PA. 22nd ed., 2010. Except insofar as any conventional excipient is incompatible with the active ingredient, its use in the pharmaceutical compositions is contemplated. Moreover, for animal (e.g., human) administration, it will be understood that preparations should meet sterility, pyrogenicity, general safety and purity standards as required by FDA Office of Biological Standards.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazopeak quaternary ammonium salts, and mixtures thereof.

The parenteral formulations will typically contain from about 20 to about 30% by weight of sepiapterin, or a pharmaceutically acceptable salt thereof, in solution. Suitable preservatives and buffers can be used in such formulations. In order to minimize or eliminate irritation at the site of injection, such compositions may contain one or more nonionic surfactants having a hydrophilic-lipophilic balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Sepiapterin, or a pharmaceutically acceptable salt thereof, of the present invention may be made into injectable formulations. The requirements for effective pharmaceutical excipients for injectable compositions are well known to those of ordinary skill in the art. See *Remington: The Science and Practice of Pharmacy*, 22$^{nd}$ *Edition*, Lippincott Williams & Wilkins, (2012); and *Encyclopedia of Pharmaceutical Technology*, eds. J. Swarbrick and J. C. Boylan, 2006, Marcel Dekker, New York, each of which is incorporated herein by reference Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains sepiapterin, or a pharmaceutically acceptable salt thereof, and a suitable vehicle or excipient. It may also contain other components, such as an anti-irritant. The excipient can be a liquid, solid or semisolid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Sepiapterin, or a salt thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Additionally, the sepiapterin, or a pharmaceutically acceptable salt thereof, may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such excipients as are known in the art to be appropriate.

Solid Dosage Form for Oral Administration

Formulations for oral use include particles containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, anti-adhesives (e.g., magnesium stearate, zinc stearate, stearic acid, silicas, hydrogenated vegetable oils, or talc), and anti-caking agents (e.g., colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, polydimethylsiloxane). Other pharmaceutically acceptable excipients can be colorants, flavoring agents, plasticizers, humectants, and buffering agents. In some embodiments, excipients (e.g., flavoring agents) are packaged with the composition. In some embodiments, excipients (e.g., flavorings) are packaged separately from the composition (e.g., are combined with the composition prior to administration).

The solid compositions of the invention may include a coating adapted to protect the composition from unwanted chemical changes, (e.g., chemical degradation prior to the release of the active substances). The coating may be applied on the solid dosage form in a similar manner as that described in *Encyclopedia of Pharmaceutical Technology*, supra.

Powders and granulates may be prepared using the ingredients mentioned above in a conventional manner using, e.g., a mixer, a fluid bed apparatus, melt congeal apparatus, rotor granulator, extrusion/spheronizer, or spray drying equipment.

Methods of Treatment

Sepiapterin may serve as a useful therapeutic for diseases associated with low intracellular BH4 levels or with dysfunction of various BH4 dependent metabolic pathways including, but not limited to, primary BH4 deficiency, GTPCH deficiency, 6-pyruvoyl-tetrahydropterin synthase (PTPS) deficiency, DHPR deficiency, sepiapterin reductase deficiency, dopamine responsive dystonia, Segawa Syndrome, tyrosine hydroxylase deficiency, phenylketonuria, DNAJC12 deficiency, Parkinson's Disease, depression due to Parkinson's Disease, impulsivity in Parkinson's patients, major depression, Autism spectrum, ADHD, schizophrenia, Bipolar disorder, cerebral ischemia, restless leg syndrome, Obsessive Compulsive Disorder, anxiety, aggression in Alzheimer's disease, cerebrovascular disorders, spasm after subarachnoidal hemorrhage, myocarditis, coronary vasospasm, cardiac hypertrophy, arteriosclerosis, hypertension, thrombosis, infections, endotoxin shock, hepatic cirrhosis, hypertrophic pyloric stenosis, gastric mucosal injury, pulmonary hypertension, renal dysfunction, impotence, and hypoglycemia. Thus, the various forms of sepiapterin, or a salt thereof, in accordance with the present invention can be administered to a patient in an effective amount to obtain a treatment or amelioration of the disease, disorder or condition.

In some embodiments of any of the foregoing methods, the food is a high protein food. In some embodiments of any of the foregoing methods, the food is a high fat food (e.g., at least 25, 30, 40, or 50% of the calories are from fat). In some embodiments of any of the foregoing methods, the food is a high protein and high fat food. In some embodiments, the food is high calorie food (e.g., the food includes at least 100 calories, e.g., at least 200 calories, at least 300 calories, at least 400 calories, at least 500 calories, e.g., 500-1500 or 800-1000 calories). In some embodiments of any of the foregoing methods, the food is a meal, e.g., breakfast, lunch, or dinner.

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In some embodiments, patients receive 2.5 mg/kg/day, 5 mg/kg/day 10 mg/kg/day 20 mg/kg/day, 40 mg/kg/day, 60 mg/kg/day, or 80 mg/kg/day. Patients may receive the pharmaceutical composition including sepiapterin once daily, twice daily or three times daily during treatment In some embodiments, patients continue their other current medications for BH4-related disorder (e.g., L-dopa/carbidopa, 5HTP, melatonin, MAO inhibitors, and dopamine receptor agonists as prescribed) except for BH4 supplementation (if they are taking BH4). Patients may not be permitted to take any drugs known to inhibit folate synthesis (e.g., methotrexate, pemetrexed, or trimetrexate).

In some embodiments, patients who are taking BH4 discontinue administration of BH4 (i.e., BH4 washout). Blood samples for Phe concentrations may be obtained during the BH4 washout period at 7, 5, 3, and 1 day before the treatment with the pharmaceutical composition of the invention or until blood Phe levels are >360 μmol/L at any time point during BH4 washout. In some embodiments, pre-dose blood samples are tested for sepiapterin, Phe, BH4, and tyrosine (Tyr).

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any compound; any method of production; any method of use; etc.) can be excluded from any one or more claims, for any reason, whether or not related to the existence of prior art.

EXAMPLES

Example 1. Evaluation of the Food Effect on the Administration of Sepiapterin

Method: Subjects received 2 oral doses of sepiapterin (10 mg/kg) separated by 1 week in a fasted and fed state. Subjects were fed a standard high-fat (approximately 50 percent of total caloric content of the meal) and high-calorie (approximately 800 to 1000 calories) meal starting 30 minutes prior to receiving their second oral dose of sepiapterin on Day 8.

Sampling for PK analysis occurred predose on Days 1 and 8 (within 30 minutes before dosing) and 0.5 hr, 1 hr, 2 hr, 4 hr, 8 hr, 12 hr, and 24 hr after the doses on Days 1 and 8. The blood concentrations of sepiapterin and BH4 were analyzed by MNG Labs.

The cerebrospinal fluid (CSF) of selected subjects is collected via lumbar puncture on Day1 (before dose) and on Day 7 (i.e., following daily dosing for 7 days) approximately 30 minutes from time of the maximum observed plasma BH4 concentration (Tmax) as determined from the blood analysis.

The cerebral spinal fluid (CSF) is analyzed by MNG Labs. Descriptive statistics are provided to characterize any changes in neurotransmitter metabolism between the Day 1, and Day 7 sample results.

Results: As shown in Tables 1 and 2 below and FIG. 1, surprisingly, the Cmax of BH4 in the plasma was much higher in subjects when fed prior to administration compared to subjects who had fasted prior to administration.

Further, there was a decrease in plasma sepiapterin concentration but an increase in BH4 concentration, when sepiapterin was administered in the fed vs. fasting state (FIG. 1). Geometric mean ratios (fasted/fed, 90% CI) for plasma sepiapterin were 1.29 (0.84 to 2.00) for $AUC_{last}$ and 1.57 (1.21 to 2.0) for Cmax. Corresponding ratios (90% CI) for plasma BH4 were 0.58 (0.47 to 0.71) for $AUC_{0-inf}$ and 0.55 (0.45 to 0.68) for Cmax. Overall exposure to BH4 as measured by $AUC_{0-inf}$ and $AUC_{last}$ increased by 1.7-fold when sepiapterin was administered in the fed state compared with the fasted state.

TABLE 1

Summary of BH4 Concentration in Plasma of Fasted Subjects

| | Time (hours) | | | | | | | |
|---|---|---|---|---|---|---|---|---|
| | 0 | 0.5 | 1 | 2 | 4 | 8 | 12 | 24 |
| Mean (nM) | 7.62 | 25.65 | 154.63 | 413.48 | 624.34 | 248.09 | 85.87 | 18.33 |
| SD (nM) | 1.26 | 14.20 | 42.65 | 104.49 | 210.24 | 118.04 | 39.26 | 8.65 |
| Median (nM) | 7.75 | 22.85 | 147.30 | 370.40 | 635.05 | 232.55 | 75.30 | 15.35 |
| Minimum (nM) | 5.00 | 13.80 | 98.50 | 271.40 | 379.00 | 90.20 | 38.90 | 8.50 |
| Maximum (nM) | 9.00 | 66.50 | 223.10 | 617.90 | 1127.90 | 457.30 | 162.00 | 37.40 |

TABLE 2

Summary of BH4 Concentration in Plasma of Fed Subjects

| | Time (hours) | | | | | | | |
|---|---|---|---|---|---|---|---|---|
| | 0 | 0.5 | 1 | 2 | 4 | 8 | 12 | 24 |
| Mean (nM) | 8.43 | 33.32 | 165.79 | 586.90 | 1098.85 | 520.33 | 161.39 | 19.27 |
| SD (nM) | 1.45 | 21.70 | 82.02 | 249.26 | 289.74 | 192.50 | 58.43 | 8.20 |
| Median (nM) | 8.50 | 30.95 | 160.00 | 554.00 | 1010.60 | 485.00 | 142.30 | 16.15 |
| Minimum (nM) | 6.00 | 8.90 | 42.30 | 298.90 | 750.80 | 252.70 | 90.40 | 12.10 |
| Maximum (nM) | 11.00 | 76.40 | 369.00 | 1199.90 | 1566.70 | 926.30 | 261.10 | 40.10 |

Figure 2:
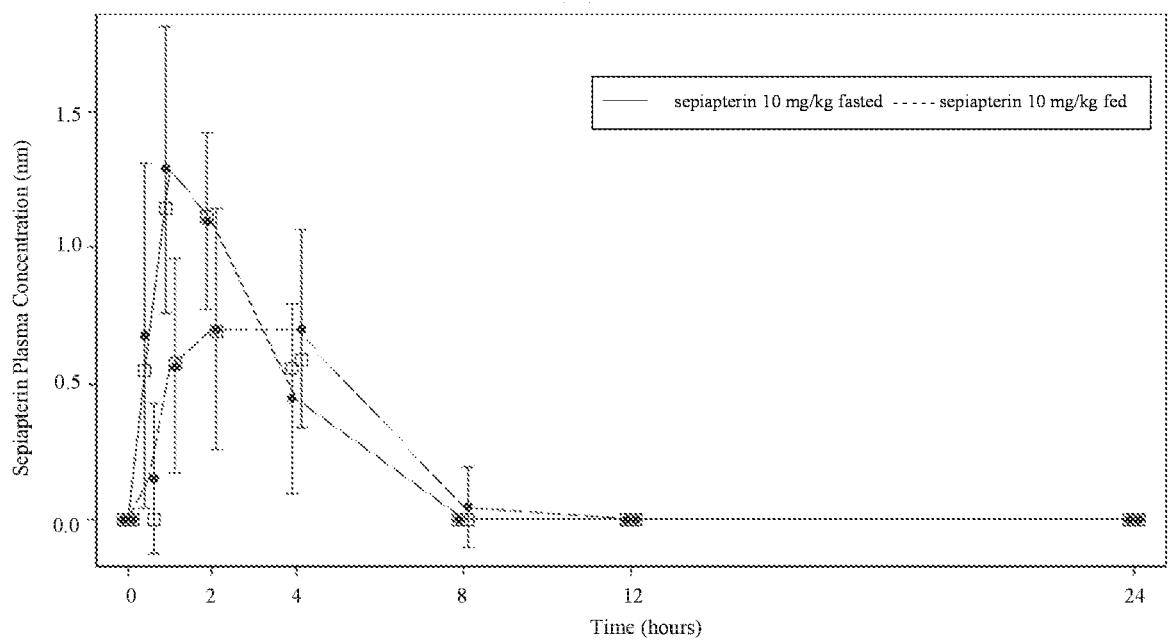
FIG. 2 is a graph illustrating the mean plasma concentration of sepiapterin over time in fed and fasted subjects.

Further, as shown in Tables 3 and 4 below and FIG. 2, surprisingly, the Cmax of sepiapterin in the plasma was much lower in subjects when fed prior to administration compared to subjects who fasted prior to administration.

TABLE 3

Summary of Sepiapterin Concentration in Plasma of Fasted Subjects

| | Time (hours) | | | | | | | |
|---|---|---|---|---|---|---|---|---|
| | 0 | 0.5 | 1 | 2 | 4 | 8 | 12 | 24 |
| Mean (nM) | 0 | 2.85 | 5.43 | 4.63 | 1.88 | 0 | 0 | 0 |
| SD (nM) | 0 | 2.67 | 2.22 | 1.36 | 1.48 | 0 | 0 | 0 |
| Median (nM) | 0 | 2.32 | 4.82 | 4.71 | 2.37 | 0 | 0 | 0 |
| Minimum (nM) | 0 | 0 | 3.15 | 2.52 | 0 | 0 | 0 | 0 |
| Maximum (nM) | 0 | 7.23 | 10.19 | 6.65 | 3.93 | 0 | 0 | 0 |

TABLE 4

Summary of Sepiapterin Concentration in Plasma of Fed Subjects

| | Time (hours) | | | | | | | |
|---|---|---|---|---|---|---|---|---|
| | 0 | 0.5 | 1 | 2 | 4 | 8 | 12 | 24 |
| Mean (nM) | 0 | 0.63 | 2.38 | 2.96 | 2.96 | 0.18 | 0 | 0 |
| SD (nM) | 0 | 1.17 | 1.66 | 1.88 | 1.53 | 0.63 | 0 | 0 |
| Median (nM) | 0 | 0 | 2.42 | 2.91 | 2.50 | 0 | 0 | 0 |
| Minimum (nM) | 0 | 0 | 0 | 0 | 0 | 0 | 0 | 0 |
| Maximum (nM) | 0 | 3.22 | 4.57 | 5.92 | 5.56 | 2.19 | 0 | 0 |

Example 2. Comparison of Adverse Events in Fed and Fasted Subjects

Method: Twelve subjects were given a single dose (10 mg/kg) of sepiapterin under fasting conditions and then 7 days later under fed conditions. Standard definitions of adverse events (AE) were used. All-cause AE were those that occurred at any time; treatment-emergent adverse events (TEAE) were those that occurred at or after the time of administration of study treatment. TEAEs related to study drug were based on the opinion of the investigator. Serious AE were defined as life threatening or caused death, hospitalization or prolongation of existing hospitalization, or were a persistent or significant disability/incapacity or a substantial disruption of the ability to conduct normal life functions, or a congenital anomaly/birth defect.

Results: As shown in Table 5, surprisingly, there was a decreased incidence of adverse events when sepiapterin was administered to fed subjects compared to fasted subjects.

TABLE 5

Comparison of adverse events in fasted and fed conditions

| | Sepiapterin 10 mg/kg | |
|---|---|---|
| | Fasted | Fed |
| ≥1 AE | 5 | 1 |
| TEAE | 4 | 1 |
| TEAE related to study drug | 1 | 0 |

Example 3. Determination of CSF Levels of Neurotransmitters after Administration of Sepiapterin Method: Analyses were conducted in CSF samples of subjects administered 60 mg/kg sepiapterin or placebo. The following analytes were measured: sepiapterin, BH4, BH2, homovanillic acid (HVA), and 5-hydroxyindoleacetic acid (HIAA). Descriptive (n, mean, SD, median, minimum, maximum) statistics for these analytes at Day 1 and Day 7+/−30 minutes from $T_{max}$ and change from baseline at Day 7 were determined for each analyte.

Results: Sepiapterin was not detected in the CSF on Day 1 or Day 7+/−30 minutes from BH4 $T_{max}$. The CSF concentration of BH4 increased by 4.102 ng/mL in sepiapterin-treated subjects while it did not change in subjects receiving placebo (change from baseline of −0.010 ng/mL). Similarly, the CSF concentration of BH2 increased by 1.368 ng/mL in sepiapterin-treated subjects while it did not change in subjects receiving placebo (change from baseline of −0.020 ng/mL).

Changes in neurotransmitter concentrations relative to Day 1 also differ between sepiapterin-treated subjects and subjects receiving placebo. The concentration of HVA increased by 1.378 ng/mL in sepiapterin-treated subjects compared with a decrease of 0.630 ng/mL in subjects receiving placebo. The concentration of 5-HIAA decreased in both arms but to a lesser extent in sepiapterin-treated subjects than in subjects receiving placebo (−1.142 ng/mL versus −2.440 ng/mL).

Of note, Day 1 pre-dose HVA (10.02 ng/ml) and 5-HIAA (3.69 ng/mL) concentrations for one subject were approximately a third of the concentrations observed in the other subjects (HVA: 22.45 ng/mL to 44.72 ng/mL; 5-HIAA: 9.49 ng/mL to 19.70 ng/mL). On Day 7, however, HVA (29.93 ng/mL) and 5-HIAA (9.53 ng/mL) concentrations for this subject were close to the range observed in the other sepiapterin administered subjects (HVA: 30.64 ng/mL to 43.19 ng/mL; 5-HIAA: 10.10 ng/mL to 21.59 ng/mL). HVA and 5-HIAA concentrations for the subject on Day 7 were both higher than the mean concentrations for Day 7 placebo-treated subjects. The data is summarized in Table 6 below.

TABLE 6

Analyte concentrations in the CSF of subjects.

| Analyte | Day | Treatment | Mean Concentration (ng/mL) |
|---|---|---|---|
| 5-HIAA | 1 | sepiapterin | 14.6 |
|  |  | placebo | 11.9 |
|  | 7 | sepiapterin | 13.4 |
|  |  | placebo | 9.5 |
| BH2 | 1 | sepiapterin | 0.5 |
|  |  | placebo | 0.5 |
|  | 7 | sepiapterin | 1.9 |
|  |  | placebo | 0.5 |
| BH4 | 1 | sepiapterin | 4.4 |
|  |  | placebo | 3.2 |
|  | 7 | sepiapterin | 8.5 |
|  |  | placebo | 3.2 |
| HVA | 1 | sepiapterin | 32.3 |
|  |  | placebo | 25.1 |
|  | 7 | sepiapterin | 33.7 |
|  |  | placebo | 24.5 |
| Sepiapterin | 1 | sepiapterin | 0 |
|  |  | placebo | 0 |
|  | 7 | sepiapterin | 0 |
|  |  | placebo | 0 |

Example 4. Pharmacokinetic Analysis of Administration of Multiple Doses of Sepiapterin Methods: Three cohorts of eight fed subjects each were randomized to receive once-daily sepiapterin or placebo for 7 days in a 6:2 ratio. A sentinel dose strategy was also used for administration of the highest sepiapterin dose.

Results: Plasma-time concentrations of sepiapterin and BH4 were similar after 1 and 7 days of treatment with sepiapterin, with no drug accumulation. The pharmacokinetic data is shown in Table 7 below.

TABLE 7

Summary of pharmacokinetic data for multiple administrations of sepiapterin

| Parameter | Compound | Day | Dose of sepiapterin (mg/kg) | | |
|---|---|---|---|---|---|
| | | | 5 | 20 | 60 |
| $C_{max}$ (ng/mL) | sepiapterin | 1 | 0.6 | 1.2 | 2.7 |
|  |  | 7 | 0.6 | 1.3 | 2.8 |
|  | BH4 | 1 | 147 | 496 | 597 |
|  |  | 7 | 152 | 516 | 678 |
| $T_{max}$ (h) | sepiapterin | 1 | 3.0 | 2.6 | 3.3 |
|  |  | 7 | 3.0 | 2.7 | 3.0 |
|  | BH4 | 1 | 4.0 | 4.0 | 4.6 |
|  |  | 7 | 4.0 | 4.0 | 4.0 |
| $AUC_{0-24}$ (ng · h/mL) | sepiapterin | 1 | NC | NC | 23 |
|  |  | 7 | NC | NC | 23 |
|  | BH4 | 1 | 994 | 3031 | 4560 |
|  |  | 7 | 1070 | 3718 | 4864 |
| $AUC_{0-inf}$ (ng · h/mL) | sepiapterin | 1 | 1.0 | 3.9 | 21.2 |
|  |  | 7 | 0.7 | 4.3 | 16.0 |
|  | BH4 | 1 | 1014 | 3085 | 4668 |
|  |  | 7 | NC | NC | NC |

NC = Not calculated

Other Embodiments

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

What is claimed:

1. A method of therapeutic treatment of a BH4-related disorder in a subject in need thereof, the method comprising administering to the subject an effective amount of sepiapterin, or a pharmaceutically acceptable salt thereof, with food,
   wherein the BH4-related disorder is a BH4 deficiency, high plasma phenylalanine, or phenylketonuria.

2. The method of claim 1, wherein the effective amount is an amount sufficient to produce a concentration of at least 50 ng/ml in the plasma of the subject within 10 hours of administration.

3. The method of claim 2, wherein the effective amount comprises a dose that is at least 20% lower than the dose sufficient to produce a maximum BH4 plasma concentration (Cmax) of at least 50 ng/mL in the plasma of the subject within 10 hours of administration of sepiapterin, or a pharmaceutically acceptable salt thereof, without food.

4. The method of claim 1, wherein the effective amount is 2.5 mg/kg to 100 mg/kg per dose.

5. The method of claim 1, wherein the administration to the subject occurs less than 30 minutes prior to consuming food.

6. The method of claim 1, wherein the administration to the subject is substantially at the same time as food.

7. The method of claim 1, wherein the administration is immediately after the consumption of food up to 2 hours after the consumption.

8. The method of claim 1, wherein the effective amount results in an increase in the maximum plasma concentration (Cmax) of BH4 compared to administration without food.

9. The method of claim 1, wherein the effective amount results in an increase in the area under the concentration time curve from time zero to last concentration ($AUC_{0\text{-}last}$) of BH4 compared to administration without food.

10. The method of claim 1, wherein the BH4-related disorder is a BH4 deficiency.

11. The method of claim 10, wherein the BH4 deficiency is primary BH4 deficiency.

12. The method of claim 1, wherein the BH4-related disorder is phenylketonuria.

13. The method of claim 1, wherein the BH4-related disorder is high plasma phenylalanine.

* * * * *

UNITED STATES PATENT AND TRADEMARK OFFICE
CERTIFICATE OF CORRECTION

PATENT NO. : 12,257,252 B2
APPLICATION NO. : 17/059632
DATED : March 25, 2025
INVENTOR(S) : Neil Smith et al.

Page 1 of 1

It is certified that error appears in the above-identified patent and that said Letters Patent is hereby corrected as shown below:

In the Specification

Column 7, Lines 49-57, replace "Sepiapterin has the structure:

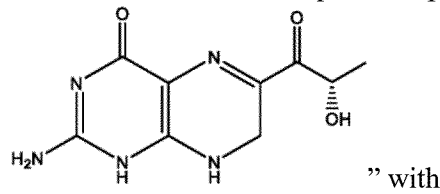

" with

-- Sepiapterin has the structure:

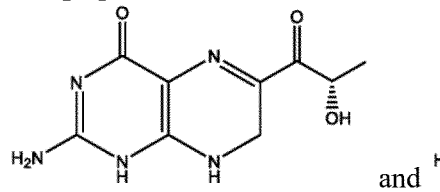 and 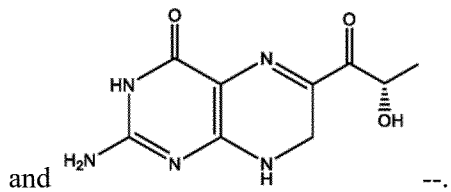 --.

Signed and Sealed this
Sixteenth Day of September, 2025

Coke Morgan Stewart
*Acting Director of the United States Patent and Trademark Office*